United States Patent [19]

Antonucci

[11] Patent Number: 4,832,745
[45] Date of Patent: May 23, 1989

[54] NON-AQUEOUS DENTAL CEMENTS BASED ON DIMER AND TRIMER ACIDS

[75] Inventor: Joseph M. Antonucci, Kensington, Md.

[73] Assignee: The United States of America as represented by the Secretary of the Department of Health and Human Services, Washington, D.C.

[21] Appl. No.: 922,811

[22] Filed: Oct. 16, 1986

Related U.S. Application Data

[63] Continuation of Ser. No. 712,102, Mar. 14, 1985, abandoned.

[51] Int. Cl.$^4$ ............................................. C09K 3/00
[52] U.S. Cl. ................................. 106/35; 433/199.1; 433/228.1; 523/116; 524/432; 524/433
[58] Field of Search .................. 106/35; 433/199, 228; 523/116; 524/432, 433

[56] References Cited

U.S. PATENT DOCUMENTS

| | | | |
|---|---|---|---|
| 3,028,247 | 4/1962 | Molnar | 106/35 |
| 3,837,865 | 9/1974 | Pellico | 106/35 |
| 4,161,410 | 7/1979 | Pellico | 106/35 |
| 4,235,633 | 11/1980 | Tomioka et al. | 106/35 |

Primary Examiner—Amelia Burgess Yarbrough
Attorney, Agent, or Firm—Browdy & Neimark

[57] ABSTRACT

Non-aqueous polycarboxylic acids such as dimer and trimer acids are reacted with a variety of polyvalent metal bases to yield a new, versatile class of cements. Many of these cements have unique energy-absorbing properties and excellent dimensional stability yielding mechanically tough and ductile materials. They also do not inhibit the polymerization of resin-based dental materials and thus can be formulated to yield hybrid resin-composite-cement materials. The bulky, hydrophobic nature of these acids with their relatively low carboxylic content results in cements that are low shrinking, hydrolytically resistant and biocompatible.

14 Claims, 3 Drawing Sheets

SCHEMATIC STRUCTURE OF DIMER MOLECULE

SCHEMATIC STRUCTURE OF TRIMER MOLECULE

FIG. 1.
(PRIOR ART)

Monoacid        Base            "insoluble soap matrix"

BASES: M = Zn, Mg, etc. oxides, hydroxides, carbonates

FIG. 3.

ACRYLIC

Monocyclic                                   Bicyclic

SCHEMATIC STRUCTURE OF DIMER MOLECULE

SCHEMATIC STRUCTURE OF TRIMER MOLECULE

NON-AQUEOUS DENTAL CEMENTS BASED ON DIMER AND TRIMER ACIDS

This application is a continuation of application Ser. No. 712,102, filed Mar. 14, 1985, now abandoned.

BACKGROUND OF THE INVENTION

This invention relates generally to dental compositions and more particularly to dental cements based on dimer and trimer acids.

Figure 1:
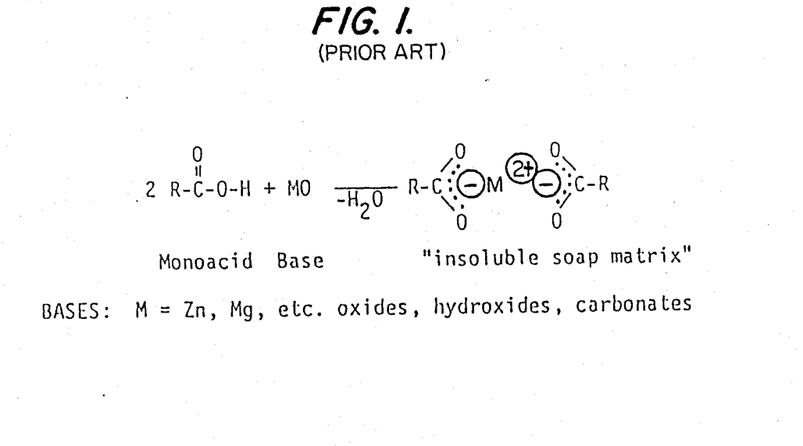
FIG. 1 shows the formation of divalent metal carboxylate cements from non-chelating monocarboxylic acis.

Researchers, in a quest for a non-eugenol cement, have demonstrated the ability of many non-chelating, monocarboxylic acids in a liquified state to form coherent, cementitious products on admixture with divalent metal oxides or hydroxides. The matrix of these monocarboxylate cements probably consists of a loose association of the divalent metallic carboxylate salt which, depending on the nature of the carboxylate anion, may have resinous or amorphous qualities (FIG. 1). Relatively high molecular weight monobasic acids yielded cements of low solubility and water-repellancy. However, probably because of the nature of the binder, these cements were mechanically weak, especially after exposure to water at 37° C.

Figure 2:
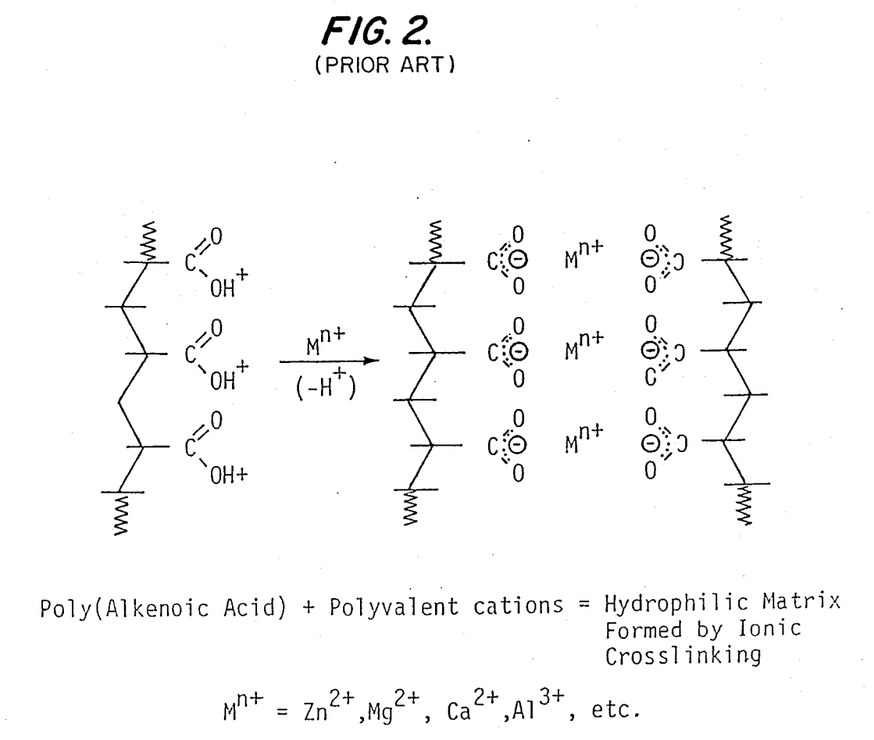
FIG. 2 shows an idealized mechanism for the setting of aqueous polycarboxylate-based dental materials.
Figure 3:
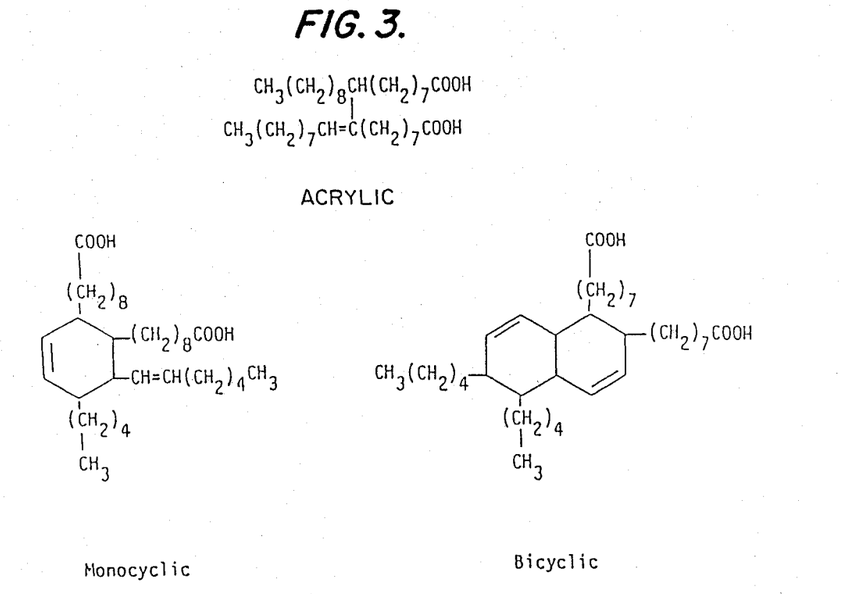
FIG. 3 shows the possible isomeric structures of dimer acids.

By contrast, the conventional polycarboxylate-based cements (i.e. zinc polycarboxylate and glass ionomer cements) derived from aqueous solutions of poly(alkenoic) acids and basic inorganic powders with leachable polyvalent cations, are much stronger materials. The matrices of these cements, which contain considerable amounts of water, are formed primarily by a series of ionic cross-linking reactions involving the pendant carboxyl groups of the polyelectrolyte and polyvalent cations displaced from the base powder by the acid solution. The resulting polymeric binders are relatively rigid and hydrophilic, i.e. they are stiff hydrogels (FIG. 2).

In U.S. Pat. Nos. 3,837,865 and 4,161,410, both to Pellico, a $C_{36}$ dimer acid or a $C_{54}$ trimer acid is mixed with zinc oxide or a mixture of zinc oxide and MgO to produce a dental composition. Powder to liquid ratios of up to 4 are disclosed. Because of these low powder to liquid ratios (P/L), the substances were somewhat flexible and not suitable for all dental cement applications. At higher P/L ratios, brittle fracture was expected. Furthermore, the compositions of Pellico and most dental compositions tend to contract upon setting. This contraction present serious difficulties when the cement is intended for many dental applications.

SUMMARY OF THE INVENTION

It is an object of the present invention to provide a strong dental cement which does not undergo brittle fracture.

It is another object of the present invention to provide a dental cement which is hydrophobic.

It is a further object of the present invention to provide a dental cement which is less ionic, hydrophobic and resistant to deformation under compression and brittle fracture.

It is yet another object of the present invention is to develop useful cements having polymeric matrices of much less rigidity and hydrophilicity than prior art dental cements by acid-base, chain-extending reactions of dimer (DA) and trimer (TA) acids with a variety of polyvalent bases.

These and other objects are achieved by the reaction product of dimer and/or trimer carboxylic acids with a select group of bases and/reactive and non-reactive fillers. The reaction may be carried out at ambient temperatures.

DESCRIPTION OF THE PREFERRED EMBODIMENTS

Preferably, the dental composite formulation comprises the reaction product of a dimer and/or trimer carboxylic acid and a base and/or filler.

The base and/or filler (i.e., the powder component) may be SrO or binary mixtures of ZnO and $ZrO_2$, ZnO and $CaSiO_3$; ZnO and ethylene acrylic acid copolymer 5 (PEAA), $Ca(OH)_2$ and tribasic calcium phosphate; $Ca(OH)_2$ and MgO; $Ca(OH)_2$ and $TiO_2$, $Ca(OH)_2$ and ZnO, ZnO and $TiO_2$, $Ca(OH)_2$ and SrO, ZnO and SrO, or ZnO and $Al_2O_3$. If ZnO is used, the powder is preferably micronized. All percentages and ratios referred to herein are by weight, unless otherwise stated. Additional fillers may be included in the mixtures used.

For both binary and ternary powder components, a wide range of compositions and powder-liquid ratios may be used. As more of the powder component comprises a powder of a small volume-weight ratio, such as ZnO, a greater P/L ratio may be employed. For example, with a 10% $Ca(OH)_2$-90% ZnO powder component, a P/L ratio of 7 may be used.

A ternary powder component comprising $Ca(OH)_2$, MgO and ZnO may also be employed, with excellent results. If a ternary, rather than binary, powder component is used, then a P/L ratio of from between 1 and 8 and preferably between 1 and 9 should be used. The actual P/L ratio used is dependent upon the amounts $Ca(OH)_2$ and ZnO present. Higher P/L ratios may be used depending upon the amounts of $Ca(OH)_2$ and ZnO used. In general, larger percentages of $Ca(OH)_2$ require the use of a lower P/L ratio, while larger percentages of ZnO allow the use of a higher P/L ratio. In general, for any one powder, higher P/L ratios decrease the tendancy of the composition to contract upon setting.

Additional fillers may be included within the unitary, binary or ternary powder component.

Preferably, when a ZnO-containing powder (except when mixed with PEAA or $Ca(OH)_2$) is used, ZnO is about 20–90 weight percent of the powder, and a powder to liquid ratio of greater than 4, and preferably at least 5, up to at least 10, is used. When ZnO is mixed with PEAA in a powder, ZnO should be about 92–80 weight percent of the powder. The use of PEAA as a filler does not significantly affect the preferred powder/liquid (P/L) ratio.

The dimer acids are $C_{36}$ dimer acids and the trimer acids are $C_{54}$ acids. These acids are formed by joined units of $C_{18}$ acids.

The powder and the acids used may be mixed as a powder-liquid or as a powder-paste with similar results. The powder-liquid ratios discussed refer to the total amount of powder present, whether first mixed with liquid (i.e. dimer or trimer acid) or not. Obviously, only non-reactive fillers may be used to form a paste from the liquid. For the sake of convenience, the term "powder component" refers to all powder present, reactive and non-reactive, whether a portion thereof is mixed with liquid or not.

$Ca(OH)_2$ may be made less reactive by heating, to increase setting times to workable limits. When this deactivated $Ca(OH)_2$ is used, a larger percent of $Ca(OH)_2$ may be present in the powder component without so shortening the setting time that the powder becomes unworkable.

MATERIALS AND METHODS

I. Materials

A. Liquid Polyacids

Figure 4:
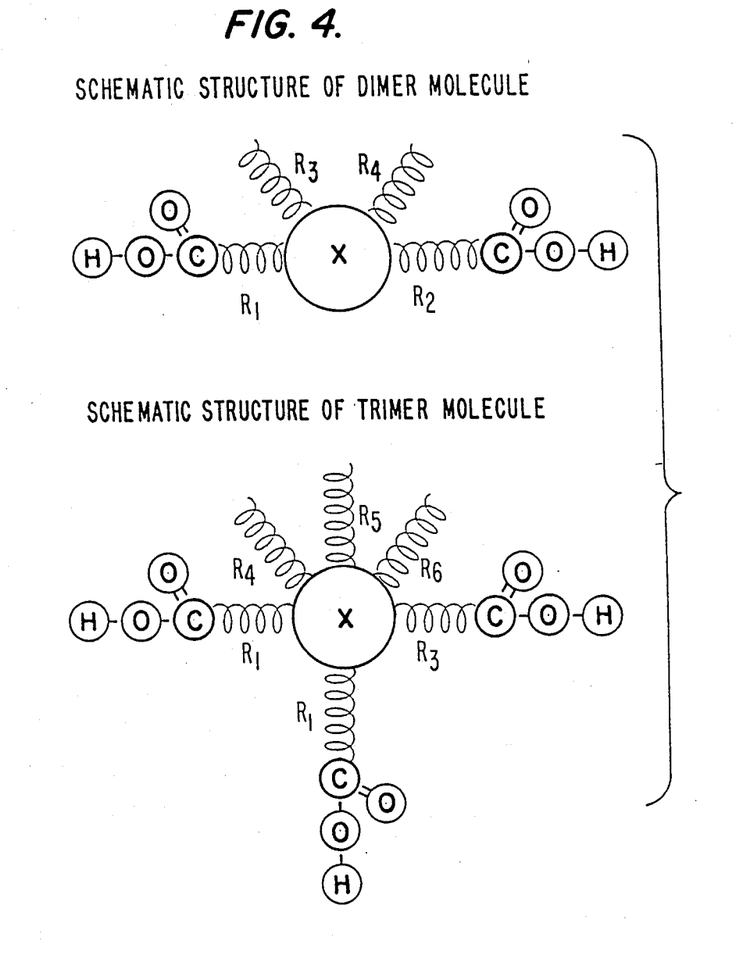
FIG. 4 schematically shows dimeric and trimeric structures where the R group is an alkyl side chain.

Dimer (DA) and trimer (TA) acids are designations for the moderately viscous, liquid products obtainable from the polymerization of certain unsaturated $C_{18}$ fatty acids (e.g. oleic, linoleic, etc.). The exact chemical structures of DA and TA are somewhat uncertain as they each consist of complex isomeric mixtures of $C_{36}$ diacids and $C_{54}$ triacids. Some 3. Schematic structures of DA and TA are shown in FIG. 4 where the R groups are alkyl side chains. The unique properties of these polyacids, such as their room temperature, workable liquidity and their bulky flexible hydrophobic core structures terminating in 2 or 3 carboxyl groups, suggested their use as the acid component of this new type of cement.

For this study the purest grade of a commercially available DA was used (1010 Empol dimer acid, Emery Industry, Inc., Cincinnati, OH). This grade of DA has 97% DA and 3% TA and extremely low redisual unsaturation. The TA used was a grade that consisted of 90% TA and 10% DA (Empol 1041). The average molecular weights were 565 and 850 for DA and TA, respectively.

B. Base Powders

The base powders used in this study are listed in Table A with their names, chemical formulas, grades and sources. Some of the base powders (CaO, MgO, ZnO) of reagent grade required activation by ball milling and/or exposure to small amounts of certain carboxylic acids (e.g. acetic, propionic). Typical procedures for these surface treatments of the bases are outlined below.

ACTIVATION BY BALL MILLING

Reagent grade CaO and MgO were activated by centrigual ball milling in ethanol for 24 and 48 h, respectively. (Pulverisette 6, Tekmar, Cincinnati, OH.

ACTIVATION BY ACID PRETREATMENT

The various reagent grade oxides (CaO, ZnO, MgO) were activated by surface treatment of these powders with organic solvents such as hexane, cyclohexane, dichloromethane, acetone, etc., which contained small amounts (e.g. 0.5-2.0%) of monobasic acids such as acetic, proprionic acid, etc. After mixing in a flask for 15 mins., the solvent was removed by simple rotary evaporation procedures.

C. Fillers

The fillers used in this study are listed in Table B with their names, chemical formulas or acronyms, grades and sources.

D. Cement Evaluations

The setting times, compressive strengths, and, in some cases, the solubilities of the new cements were determined according to the respective tests of ANSI/ADA Specification No. 30 for Dental zinc Oxide-Eugenol Type Restorative Materials. The diametral tensile strengths of cylindrical specimens, 6 mm $\times 12$ mm, were measured with a universal testing machine at a loading rate of 5 mm/min. In a few cases the 24 h solubility of the cement was determined in 1 M lactic acid (neutralized to pH $=4$).

RESULTS

The results are summarized in Tables 1-5.

SETTING CHARCTERISTICS

The reactivity of DA and TA with solid metallic hydroxides, oxides and other solid basic reactants is dependent on a number of factors: the inherent basicity of the powder; its state of subdivision and the type and degree of surface activation or modification. Of all the bases studied, $Ca(OH)_2$ appeared to be the most reactive, especially thinlayer chromatographic grades. Other grades of $Ca(OH)_2$ were not quite as reactive but could be made so by ball-milling techniques.

The order of increasing reactivity of DA with reagent grade oxides as measured by setting determinations was $CaO > MgO > ZnO >> Al_2O_3$. The first two oxides could be activated by ball milling in ethanol to give base powders having acceptable setting characteristics. Surface activation by means of acetic acid, propionic acid and other carboxylic acids also was effective. With the reagent grade ZnO ball milling in ethanol for 48 h did not activate the powder sufficiently to obtain acceptable setting times. Activation with 0.5 to 2.0% by weight of propionic acid resulted in powders having acceptable setting characteristics. A commercial micronized ZnO was a very acceptable base powder, undoubtedly because of its fine particle size. Coating reagent grade MgO with ascorbic acid or ascorbyl palmitate also seems to have an activating effect on this oxide. Although setting times were considerably reduced (e.g. from 4.5 h to 35 mins.) for mixtures of these coated oxides and DA, even shorter setting times (e.g. 6 mins.) resulted from an acetate or proprionate coating on the oxide. However, using mixtures of ascorbyl palmitate and propionic acid coated MgO with DA gave cement mixes with acceptable setting times. Other techniques for accelerating the setting behavior of DA and TA cements include the use of mixed base systems (e.g. $MgO + Ca(OH)_2$), and the addition of activators to the polybasic acids, e.g. propionic acid, 2-ethoxybenzoic acid, etc.

MECHANICAL PROPERTIES

Table I summarizes the properties of some DA/ZnO cements using ZnO as a major basic component. Formulation A using micronized ZnO resulted in a tough, strong cement with compressive (CS) and a diametral tensile strength values of about 50 and 7 MPa, respectively. Although these cements did break in compression at a crosshead speed of 1 mm/min., the fracture was more ductile in nature than brittle. Formulations D-G did not fragment under this compressive stress unless the time of stress was unduly prolonged. At higher crosshead speeds the specimens did fracture and, as expected, higher CS was obtained. For specimens that did not fracture the value of CS was derived from the maximum stress value recorded by the testing machine. In tension, all specimens of the DA/ZnO cement fractured cleanly into two halves.

Some of the properties of DA cements prepared with $Ca(OH)_2$ as the basic component are shown in Table 2. Under compressive load, the simple $DA/Ca(OH)_2$ cements (Formulations H and I) did not fracture but underwent plastic deformation resulting in a marked change in dimensions. Only a slight recovery in dimensions was noted after storage in distilled water at 37° C. for one month. Cements formulated with additional fillers such as tribasic calcium phosphate (HA), $TiO_2$, $SiO_2$, etc., had improved strength and showed only slight deformation under compressive stress. In tension all formulations broke cleanly into halves. On prolonged storage in distilled water at 37° C. (7d, 14d) $DA/Ca(OH)_2$ cements with HA as filler shows some increase in CS (Formulations J, K and L). All these cements have maintained their integrity after one year in $H_2O$ at 37° C.

The properties of some DA cements prepared with MgO as the base component are summarized in Table 3. The salient feature of the DA/MgO cements compared to the DA/ZnO and $DA/Ca(OH)_2$ types is the relatively high CS (34–58 MPa) achieved at relatively low powder/liquid ratios. Presumably, the magnesium dimerate matrix is stiffer and less yielding than that of calcium or zinc dimerate as these cements tend to fracture in compression as well as tension. As shown by formulation W, the cements maintain their integrity and strength on prolonged (7d) storage in water at 37° C.

Table 4 illustrates a hybrid type of DA cement which uses a binary base system of $Ca(OH)_2$ and MgO. Although the CS values are generally somewhat lower than those of DA/MgO, these cements have some of the energy-absorbing characteristics of the $DA/Ca(OH)_2$ cements in that they resist brittle fracture in compression but with only modest dimensional changes. In tension clean fractures are obtained. Again, prolonged storage in distilled water (7d at 37° C.) did not decrease CS. The addition of fillers further enhances dimensional stability and strength.

Table 5 summarizes some physical properties of representative cements derived from TA. As noted for the simple $DA/Ca(OH)_2$ cements, the analogous $TA/Ca(OH)_2$ cements, also undergo significant plastic deformation under compressive stress. The addition of fillers increases both the strength properties and dimensional stability. Similarly, the TA/MgO based cements have higher CS and also undergo fracture under compression. Cements derived from TA and the binary base system of $Ca(OH)_2$-MgO had both energy-absorbing properties, good dimensional stability and adequate CS and DTS values (Formulations IV and V).

SOLUBILITY

The water solubility of DA and TA cements appears to be generally low, varying with the relative solubilities of the base and/or filler components. Some representative solubility values are 1.5% for the $DA/Ca(OH)_2$ (Formulation I, Table 2); 0.9% for the $DA/Ca(OH)_2$ with 33% of HA (Formulation L, Table 2); and 0.1% for DA/ZnO, P/L=7 (Formulation A, Table 1). The last cement, when exposed to a lactic acid solution (pH=4) for 24 hours, exhibited only a 0.2% weight loss.

OPTICAL PROPERTIES

By proper selection of the base/filler component DA and TA cements with various degrees of translucency can be prepared. Some of these cements harmonize well with the appearance of enamel suggesting their potential for use as esthetic intermediate restorative materials. For example, translucent cements resulted from using calcium base powders (e.g. $Ca(OH)_2$) with fillers such as fused alumina, pyrogenic silica, and various other vitreous fillers. With magnesium base powders (e.g. MgO) less translucent cements are formed and zinc base powders (e.g. ZnO) yield opaque cements. By proper selection of filler components having refractive indices that match the cement matrix and also contain radiopaque elements (e.g. Ba, Sr) it is possible to formulate translucent, radiopaque cements.

The resinous nature of certain metallic salts of both monocarboxylic-(e.g. abietic) and dicarboxylic acids (e.g. dimer, azealic) has been recognized for some time. The polymeric nature of several divalent dimerates (e.g. zinc dimerate) prepared either at high temperatures (fusion method) or at ambient temperatures by precipitation from solution (metathesis) is also known. Researchers have prepared and characterized a well-defined series of divalent metal dicarboxylates (e.g. calcium sebacate) by both methods and designated these unique materials, halatopolymers, to denote their dual salt-like and polymeric character.

In contradistinction to the more common ionomer polymers which have pendant, crosslinked carboxylate groups, halatopolymers have carboxylate linkages in their backbone as depicted below:

Hydrophobic Backbone

Thus the setting mechanism involves a series of chain extending, acid-base reactions of the polyacid with polyvalent cations.

According to the present invention it is feasible to prepare dental cements having halatopolymeric matrices by the direct reaction of dimer acid with a variety of divalent metal base powders. The rate of setting for such halatopolymeric cements is determined by the state of subdivision, the surface character and the quantity of base powder. The moisture content of the components, the presence of accelerators or retarders and the temperature of mixing also affect the setting behavior.

Cements prepared from DA and TA with $Ca(OH)_2$ or CaO only exhibit a non-brittle but deformable nature. Compared to commercially available $Ca(OH)_2$ liners and pulp capping materials, these cements are stronger and more hydrolytically resistant. They also are alkaline in water and should provide a protective barrier against acids and other chemicals, be antibacterial, and stimulate the formation of secondary dentin. The deformable nature of these cements can be largely eliminated by the use of MgO as a secondary base and/or the addition of appropriate fillers (e.g. $Ca_5(PO_4)_3OH$, $TiO_2$, etc.). In addition to providing improved dimensional stability, these reinforcing agents can yield DA and TA cements of enhanced strength and hydrolytic durability.

DA and TA cements prepared with MgO as the sole base have a stronger but more brittle, much less deformable nature than those formulated with CaO or Ca(OH)$_2$. The use of a binary base system of Ca(OH)$_2$ and MgO results in tough, fracture-resistant cements that still provide an alkaline environment in the oral cavity. Formulations with ZnO provide tough, hydrophobic cements having less alkalinity.

Because of their bulky nature and relatively low carboxylic acid content (16%) these cements are expected to have excellent biocompatibility and to show very low contraction on setting. (Preliminary studies using a mercury dilatometric method indicate that the hardening of some of these cements is accompanied by a slight expansion; a future publication will detail these findings.) DA and TA are not corrosive and are classified as non-toxic by ingestion and are not considered to be primary skin or eye irritants.

DA and TA cements do not inhibit the free radical polymerization of resin-based dental materials and this property permits the formulation of hybridresin-composite cements. The versatile nature of these non-aqueous types of polycarboxylate cements suggests a number of dental applications: cavity liners, pulp capping materials, endodontic filling materials, periodontal dressing materials, impression materials, and esthetic, radiopaque temporary and intermediate restorative materials.

Expansion was not a major difficulty in the Ca(OH)$_2$ containing cements. These cements preferably have a P/L ratio of about 1–4, and more preferably about 2–3.

It should be noted that compositions J, K and P actually expanded upon setting. Likewise, Zn-Al$_2$O$_3$ containing composites also expanded upon setting.

Ca(OH)$_2$ has been found to activate weaker bases, such as MgO. Thus, when Ca(OH)$_2$ is employed as part of a binary base, no activator need be present.

As little as 10% MgO has been found to improve the deformation properties of Ca(OH)$_2$. MgO/DA and TA cements have been found to undergo brittle fracture. Mixtures of MgO and Ca(OH)$_2$ which impart desirable compressive strength and fracture resistance preferably include about 10–70% Ca(OH)$_2$ and a remainder of MgO. More preferably, the mixture contains about 60–40% Ca(OH)$_2$ and most preferably it contains about 50% Ca(OH)$_2$. Similar weight percentages of Ca(OH)$_2$ should be employed in other calcium containing powder components used in the present invention.

It is to be understood that the present invention is not limited to the embodiments disclosed which are illustratively offered and that modifications may be made without departing from the invention.

TABLE A
BASES AND ACTIVATORS USED IN DA AND TA CEMENTS

| Name | Formula or Acronym | Form | Source |
|---|---|---|---|
| Calcium Oxide | CaO | Powder | J. T. Baker Chem. Co. Phillipsburg, NJ |
| Calcium Hydroxide | Ca(OH)$_2$ | Powder (Thin Layer Chromatographic Grade) | J. T. Baker Chem. Co. Phillipsburg, NJ |
| Magnesium Oxide | MgO | Powder | J. T. Baker Chem. Co. Phillipsburg, NJ |
| Zinc Oxide | ZnO | Powder (Micronized) | Proco-Sol Chem. Co. Philadelphia, PA |
| Acetic Acid | AA | Liquid | Fisher Scientific Fairlawn, NJ |
| Propionic Acid | PA | Liquid | Fisher Scientific Fairlawn, NJ |

TABLE B
CEMENT ADDITIVES

| Name | Formula or Acronym | Form | Source |
|---|---|---|---|
| Tribasic Calcium Phosphate | HA | Powder | Fisher Scientific Co. Fairlawn, NJ |
| Titanium Oxide | TiO$_2$ | Powder | Fisher Scientific Co. Fairlawn, NJ |
| Calcium Metasilicate | CaSiO$_3$ | Powder | Interpace Corp. Willsboro, NY |
| Zirconia (Zirconium Dioxide) | ZrO$_2$ | Powder | Applied Ceramics, Inc. Atlanta, GA |
| Aluminum Hydroxide | Al(OH)$_3$ | Powder | Matheson, Coleman & Bell Norwood, OH |
| Aluminum Oxide | Al$_2$O$_3$ | Powder (Hydral 710) | Alcoa Chemicals Bauxite, AR |
| poly(methyl methacrylate) | PMMA | Powder | Esschem Essington, PA |
| poly(vinylidene fluoride) | PVF$_2$ | Powder (Grade 960 ES) | Penwalt Corp. Philadelphia, PA |
| Ethylene/Acrylic Acid Copolymer | PEAA | 15% Acrylic Acid | Scientific Polymer Prod. Ontario, NY |

TABLE 1
Properties of DA/ZnO Cements

| Cement | Powder Component In Powder | In Liquid | P/L Ratio w/w | Set. Time Min | 24 H. Mechanical Strength (MPa) Compressive | Diametral Tensile |
|---|---|---|---|---|---|---|
| A | ZnO[1] | — | 7 | 7.5 | 49.4 (2.1)[2] | 6.5 (0.5)[2] |
| B | ZnO[3] | — | 7 | 10.0 | 46.4 (1.0) | 5.8 (2.5) |
| C | ZnO[1](86%), MgO[4] | — | 4 | 7.0 | 46.6 (1.0) | 5.7 (0.8) |
| D[6] | ZnO[1] | ZrO$_2$(67%) | 9 | 9.5 | 46.6 (4.8) | 6.2 (0.9) |
| E[6] | ZnO[5] | CaSiO$_3$(67%) | 5 | 3.5 | 22.0 (1.0) | 8.2 (0.8) |
| F[6] | ZnO[1] | PEAA(5%) | 7 | 9.0 | 45.6 (1.3) | 5.7 (0.4) |
| G[6] | ZnO[1] | PEAA(10%) | 7 | 9.5 | 46.9 (2.2) | 5.6 (0.6) |

[1]Micronized ZnO
[2]Standard Deviation
[3]Activated with 0.5% PA
[4]Activated with 1.0% AA
[5]Activated with 2.0% PA
[6]Resisted fracture under compression at crosshead speed of 1 mm/min.

TABLE 2
Properties of DA/Ca(OH)₂ Cements

| Cement | Powder Component In Powder | In Liquid | P/L Ratio w/w | Set. Time Min | 24 H. Mechanical Strength (MPa) Compressive | Diametral Tensile |
|---|---|---|---|---|---|---|
| H | — | — | 1 | 7.5 | 26.7 (0.2)[1] | — |
| I | — | — | 1.5 | 3.0 | 24.6 (0.5) | 4.2 (0.7) |
| J | — | HA (50%) | 2 | 6.0 | 31.6 (1.0) 33.8 (1.2)[2] | 5.2 (0.4) |
| K | — | HA (33%) | 2 | 7.0 | 30.8 (1.9) | — |
| L | HA (33%) | — | 2 | 7.0 | 32.0 (0.6) 37.0 (0.5)[3] | 5.7 (0.6) |
| M | TiO₂ (50%) | — | 3 | 7.0 | 29.7 (1.1) | 5.8 (0.8) |
| N | Al(OH)₃ (50%) | — | 33 | 8.0 | 26.6 (0.2) | 4.9 (1.0) |
| O | — | Al(OH)₃ (67%) | 3 | 9.0 | 28.6 (1.8) | 5.2 (0.3) |
| P | SiO₂[4] (75%) | — | 4 | 3.0 | 26.9 (0.9) | 6.7 (0.5) |
| Q | PMMA (56%) | — | 3 | 5.0 | 23.3 (0.5) | — |

[1]Standard deviation
[2]7 day storage in distilled water at 37° C.
[3]14 days storage in distilled water at 37° C.
[4]Silanized with 2% 2-carboethoxypropylmethyldiethoxysilane and heated 4 hrs at 250° C.

TABLE 3
Properties of DA/MgO Cements

| Cement | Powder Component In Powder | In Liquid | P/L Ratio w/w | Set. Time Min | 24 H. Mechanical Strength (MPa) Compressive | Diametral Tensile |
|---|---|---|---|---|---|---|
| R | MgO[1] | — | 1 | 6.0 | 35.2 (1.0) | 3.8 (0.2) |
| S | MgO[2] | — | 2 | 35.0 | 50.2 (2.3) | 4.9 (0.4) |
| T | MgO[3] | H (50%) | 2 | 9.0 | 58.2 (2.2) | 5.3 (0.7) |
| U | MgO[3] | Al₂O₃ (50%) | 2 | 6.0 | 50.7 (0.8) | 4.9 (0.7) |
| V | MgO[3] | ZrO₂ (75%) | 4 | 6.5 | 55.1 (3.0) | 5.0 (0.7) |
| W | MgO[3] | TiO₂ (67%) | 3 | 6.0 | 55.8 (1.5) 56.6 (3.3) | 5.0 (0.6) |
| X | MgO[3] | CaSiO₃ (67%) | 3 | 7.0 | 45.2 (1.8) | 7.2 (1.0) |
| Y | MgO[3] | PMMA (60%) | 2.5 | 9.5 | 43.0 (0.3) | 3.8 (0.5) |
| Z | MgO[3] | PVF₂ (67%) | 3 | 9.0 | 33.9 (2.3) | 3.6 (0.3) |

[1]Activated with 1% AA
[2]Coated with 1% ascorbyl palmitate from CH₂Cl₂
[3]Activated with 1.5% PA
[4]7 day storage in distilled water at 37° C.

TABLE 4
Properties of DA/MgO—Ca(OH)₂ Cements

| Cement | Powder Component In Powder | In Liquid | P/L Ratio w/w | Set. Time Min | 24 H. Mechanical Strength (MPa) Compressive | Diametral Tensile |
|---|---|---|---|---|---|---|
| a | MgO (50%) & Ca(OH)₂ (50%) | — | 1 | 4.5 | 30.4 (2.2) | 3.3 (0.3) |
| b | MgO (50%) & Ca(OH)₂ (50%) | — | 1.5 | 4.0 | 34.6 (1.6) | — |
| c | MgO (60%) & Ca(OH)₂ (40%) | — | 3 | 5.5 | 43.8 (0.8) | 5.5 (0.5) |
| d | MgO (50%) & Ca(OH)₂ (50%) | HA (50%) | 2 | 6.5 | 40.5 (2.0) | 6.0 (0.9) |
| e | MgO (50%) & Ca(OH)₂ (50%) | TiO₂ (50%) | 3 | 6.5 | 47.5 (1.2) | 5.6 (1.0) |
| f | MgO (50%) & Ca(OH)₂ (50%) | CaSiO₃ (67%) | 3 | 2.5 | 34.5 (1.2) | 6.0 (0.5) |
| g | MgO (50%) & Ca(OH)₂ (50%) | Fuji II Powder (67%) | 3 | 9.0 | 32.4 (0.6) 34.7 (0.5)[1] | 6.3 (0.7) |
| h | MgO (23%), Ca(OH)₂ (23%) & PMMA (54%) | — | 5 | 5.0 | 30.4 (0.6) | 3.8 (0.5) |

[1]7 days storage in distilled water at 37° C.

TABLE 5

Properties of Trimer Acid (TA) Cements

| Cement | Powder Component In Powder | Powder Component In Liquid | P/L Ratio w/w | Set. Time Min | 24 H. Mechanical Strength (MPa) Compressive | 24 H. Mechanical Strength (MPa) Diametral Tensile |
|---|---|---|---|---|---|---|
| I | Ca(OH)$_2$ | — | 1.5 | 4.0 | 22.6 (0.5) | 3.7 (0.2) |
| II | MgO[1] | — | 2.0 | 6.0 | 27.7 (0.7) | 2.8 (0.3) |
| III | MgO[2] | TiO$_2$ (67%) | 3 | 6.0 | 60.4 (1.4) | — |
| IV | MgO (50%) & Ca(OH)$_2$ (50%) | TiO$_2$ (67%) | 3 | 10.0 | 42.9 (0.6) | 6.6 (0.5) |
| V | MgO (50%) & Ca(OH)$_2$ (50%) | HA (50%) | 2 | 9.0 | 46.7 (1.7) | 6.1 (0.6) |

[1] Activated with 1% AA
[2] Activated with 1.5% PA

What is claimed is:

1. A dental composite formulation consisting essentially of a reaction product of a liquid component selected from the group consisting of dimer and trimer carboxylic acids and a powder component selected from the group consisting of:

micronized or surface activated ZnO in a ratio of said powder component to said liquid component of about 7–10;

mixtures consisting essentially of 80–90% micronized or surface activated ZnO, the remainder being surface activated MgO, in a ratio of said powder component to said liquid component of about 4–10;

mixtures consisting essentially of about 30–40% micronized or surface activated ZnO, the remainder being ZrO$_2$, in a ratio of said powder component to said liquid component of about 9–10;

mixtures consisting essentially of about 30–40% micronized or surface activated ZnO, the remainder being CaSiO$_3$, in a ratio of said powder component to said liquid component of about 5–10;

mixtures consisting essentially of 90–95% micronized or surface activated ZnO, the remainder being ethylene/acrylic acid copolymer, in a ratio of said powder component to said liquid component of about 7–10;

mixtures consisting essentially of 10–70% Ca(OH)$_2$, the remainder being a member selected from the group consisting of tribasic calcium phosphate, TiO$_2$, Al(OH)$_3$, SiO$_4$ and poly(methylmethacrylate), in a ratio of said powder component to said liquid component of about 2–4;

surface activated MgO in a ratio of said powder component to said liquid component of about 2;

mixtures consisting essentially of about 25–50% surface activated MgO, the remainder being a member selected from the group consisting of tribasic calcium phosphate, Al$_2$O$_3$, ZrO$_2$, TiO$_2$, CaSiO$_3$, poly(methyl methacrylate) and poly(vinylidene fluoride), in a ratio of said powder component to said liquid component of about 2–4;

mixtures consisting essentially of about 50–60% MgO, the remainder being Ca(OH)$_2$, in a ratio of said powder component to said liquid component of about 1–3;

mixtures consisting essentially of about 35–40% MgO, about 25–35% Ca(OH)$_2$, the remainder being a member selected from the group consisting of tribasic calcium phosphate, TiO$_2$ and ZnO, in a ratio of said powder component to said liquid component of about 2–3; and mixtures consisting essentially of 20–30% MgO, 20–30% Ca(OH)$_2$, the remainder being poly(methyl methacrylate) in a ratio of said powder component to said liquid component of about 5.

2. A dental composite formulation consisting essentially of a reaction product of a liquid component selected from the group consisting of dimer and trimer carboxylic acids and a powder component selected from the group consisting of:

mixtures consisting essentially of 10–70% Ca(OH)$_2$, the remainder being a member selected from the group consisting of tribasic calcium phosphate, TiO$_2$, Al(OH)$_3$, SiO$_4$ and poly(methylmethacrylate), in a ratio of said powder component to said liquid component of about 2–4;

mixtures consisting essentially of about 50–60% MgO, the remainder being Ca(OH)$_2$, in a ratio of said powder component to said liquid component of about 1–3;

mixtures consisting essentially of about 35–40% MgO, about 25–35% Ca(OH)$_2$, the remainder being a member selected from the group consisting of tribasic calcium phosphate, TiO$_2$ and ZnO, in a ratio of said powder component to said liquid component of about 2–3;

mixtures consisting essentially of 20–30% MgO, 20–30% Ca(OH)$_2$, the remainder being poly(methyl methacrylate), in a ratio of said powder component to said liquid component of about 5;

mixtures consisting essentially of about 30–40% micronized or propionic acid activated ZnO, the remainder being ZrO$_2$, in a ratio of said powder component to said liquid component of about 9–10;

mixtures consisting essentially of about 30–40% micronized or propionic acid activated ZnO, the remainder being CaSiO$_3$, in a ratio of said powder component to said liquid component of about 5–10;

mixtures consisting essentially of 90–95% micronized or propionic acid activated ZnO, the remainder being ethylene/acrylic acid copolymer, in a ratio of said powder component to said liquid component of about 7–10; and mixtures consisting essentially of about 25–50% propionic acid activated MgO, the remainder being a member selected from the group consisting of tribasic calcium phosphate, Al$_2$O$_3$, ZrO$_2$, TiO$_2$, CaSiO$_3$, poly(methyl methacrylate) and poly(vinylidene fluoride), in a ratio of said powder component to said liquid component of about 2–4.

3. A dental composite formulation consisting essentially of a reaction product of a liquid component selected from the group consisting of dimer and trimer carboxylic acids and a powder component selected from the group consisting of:

mixtures consisting essentially of 10–70% Ca(OH)$_2$, the remainder being a member selected from the group consisting of tribasic calcium phosphate, TiO$_2$, Al(OH)$_3$, SiO$_4$ and poly(methylmethacrylate), in a ratio of said powder component to said liquid component of about 2–4;

mixtures consisting essentially of about 50–60% MgO, the remainder being Ca(OH)$_2$, in a ratio of said powder component to said liquid component of about 1–3;

mixtures consisting essentially of about 35–40% MgO, about 25–35% Ca(OH)$_2$, the remainder being a member selected from the group consisting of tribasic calcium phosphate, TiO$_2$ and ZnO, in a ratio of said powder component to said liquid component of about 2–3;

mixtures consisting essentially of 20–30% MgO, 20–30% Ca(OH)$_2$, the remainder being poly(methyl methacrylate) in a ratio of said powder component to said liquid component of about 5;

mixtures consisting essentially of about 30–40% micronized or surface activated ZnO, the remainder being ZrO$_2$, a ratio of said powder component to said liquid component of about 9–10;

mixtures consisting essentially of about 30–40% micronized or surface activated ZnO, the remainder being CaSiO$_{CaSiO_3}$, in a ratio of said powder to said liquid component of about 5–10;

mixtures consisting essentially of 90–95% micronized or surface activated ZnO, the remainder being ethylene/acrylic acid copolymer, in a ratio of said powder component to said liquid component of about 7–10; and mixtures consisting essentially of about 25–50% surface activated MgO, the remainder being a member selected from the group consisting of tribasic calcium phosphate, Al$_2$O$_3$, ZrO$_2$, TiO$_2$, CaSiO$_3$, poly(methyl methacrylate) and poly(vinylidene fluoride), in a ratio of said powder component to said liquid component of about 2–4.

4. The dental composite formulation of claim 2, wherein said powder component consists essentially of about 10–70% Ca(OH)$_2$, in a ratio of said powder component to said liquid component of about 2–3.

5. The dental composite formulation of claim 2, wherein said powder component consists essentially of 50–60% MgO and the remainder of Ca(OH)$_2$, the ratio of said powder component to said liquid component being about 1–3.

6. The dental composite formulation of claim 2, wherein said powder component consists essentially of said mixture consisting essentially of about 35–40% MgO, about 25–35% Ca(OH)$_2$, and a remainder being a member of the group consisting of: tribasic calcium phosphate, TiO$_2$ and ZnO, in a ratio of said powder component to said liquid component of about 2–3; and mixtures consisting essentially of 20–30% MgO, 20–30% Ca(OH)$_2$, the remainder being poly(methyl methacrylate) in a ratio of said powder component to said liquid component of about 5.

7. The dental composite formulation of claim 2, wherein said powder component consists essentially of mixtures consisting essentially of about 30–40% micronized or propionic acid activated ZnO, the remainder being ZrO$_2$, in a ratio of said powder component to said liquid component of about 9–10.

8. The dental composite formulation of claim 2, wherein said powder component consists essentially of mixtures consisting essentially of about 30–40% micronized or propionic acid activated ZnO, the remainder being CaSiO$_3$, in a powder to liquid ratio of about 5–10.

9. The dental composite formulation of claim 2, wherein said powder component consists essentially of mixtures consisting essentially of 90–95% micronized or propionic acid activated ZnO, the remainder being ethylene/acrylic acid copolymer, in a ratio of said powder component to said liquid component of about 7–10.

10. The dental composite formulation of claim 2, wherein said powder component consists essentially of mixtures consisting essentially of 10–70% Ca(OH)$_2$, the remainder being a member selected from the group consisting of tribasic calcium phosphate, TiO$_2$, Al(OH)$_3$, SiO$_4$ and poly(methyl methacrylate), in a ratio of said powder component to said liquid component of about 2–4.

11. The dental composite formulation of claim 2, wherein said powder component consists essentially of mixtures consisting essentially of about 25–50% propionic acid activated MgO, the remainder being a member selected from the group consisting of tribasic calcium phosphate, Al$_2$O$_3$, ZrO$_2$, TiO$_2$, CaSiO$_3$, poly(methyl methacrylate) and poly(vinylidene fluoride), in a ratio of said powder component to said liquid component of about 2–4.

12. The dental composite formulation of claim 2, wherein said powder component consists essentially of mixtures consisting essentially of about 50–60% MgO, the remainder being Ca(OH)$_2$, in a ratio of said powder component to said liquid component of about 1–3.

13. The dental composite formulation of claim 2, wherein said powder component consists essentially of mixtures consisting essentially of about 35–40% MgO, about 25–35% Ca(OH)$_2$, the remainder being a member selected from the group consisting of tribasic calcium phosphate, TiO$_2$ and ZnO, in a ratio of said powder component to said liquid component of about 2–3.

14. The dental composite formulation of claim 2, wherein said powder component consists essentially of mixtures consisting essentially of 20–30% MgO, 20–30% Ca(OH)$_2$, the remainder being poly(methyl methacrylate).

* * * * *